(12) United States Patent
Benedetti

(10) Patent No.: US 9,128,027 B2
(45) Date of Patent: Sep. 8, 2015

(54) APPARATUS FOR DETECTING INHOMOGENEITIES

(75) Inventor: Paolo Benedetti, San Damaso (IT)

(73) Assignee: IMAL S.R.L., San Damaso (IT)

(*) Notice: Subject to any disclaimer, the term of this patent is extended or adjusted under 35 U.S.C. 154(b) by 126 days.

(21) Appl. No.: 13/822,877

(22) PCT Filed: Sep. 12, 2011

(86) PCT No.: PCT/IB2011/053984
§ 371 (c)(1),
(2), (4) Date: Mar. 13, 2013

(87) PCT Pub. No.: WO2012/069940
PCT Pub. Date: May 31, 2012

(65) Prior Publication Data
US 2013/0298683 A1    Nov. 14, 2013

(30) Foreign Application Priority Data

Nov. 25, 2010   (IT) .............................. MO2010A0342

(51) Int. Cl.
| | |
|---|---|
| *G01N 29/04* | (2006.01) |
| *G01N 29/11* | (2006.01) |
| *G01N 29/27* | (2006.01) |
| *G01N 29/32* | (2006.01) |
| *G01N 33/46* | (2006.01) |

(52) U.S. Cl.
CPC ................ *G01N 29/04* (2013.01); *G01N 29/11* (2013.01); *G01N 29/27* (2013.01); *G01N 29/32* (2013.01); *G01N 33/46* (2013.01); *G01N 2291/0231* (2013.01); *G01N 2291/0238* (2013.01); *G01N 2291/0289* (2013.01); *G01N 2291/051* (2013.01); *G01N 2291/105* (2013.01)

(58) Field of Classification Search
CPC .............. G01N 29/221; G01N 29/223; G01N 29/2462; G01N 29/2468; G01N 2291/0231; G01N 2291/0238; G01N 2291/2632; G10K 11/004
USPC .................................... 73/617, 643, 599, 600
See application file for complete search history.

(56) References Cited

U.S. PATENT DOCUMENTS

| | | | |
|---|---|---|---|
| 6,367,330 B1 | 4/2002 | Schafer | |
| 2012/0266678 A1* | 10/2012 | Domke et al. | .................. 73/642 |

FOREIGN PATENT DOCUMENTS

| | | |
|---|---|---|
| DE | 195 19 669 C1 | 1/1997 |
| EP | 1 324 032 A1 | 7/2003 |
| EP | 1324032 A1 * | 7/2003 |

* cited by examiner

*Primary Examiner* — John Chapman, Jr.
(74) *Attorney, Agent, or Firm* — Pearne & Gordon LLP

(57) ABSTRACT

An apparatus for detecting inhomogeneities in panels (1), of the type suitable to be used for panels (1) in transit along a processing line and comprising a plurality of sound wave emitting devices (2), operating from one side of the panel (1) in transit, and a plurality of sound wave receiving devices (3), operating from the opposite side of the same panel (1) at a pre-established distance from the emitting device (2). The receiving devices (3) are situated at the ends of a plurality of channels (30), which are disposed in alignment with the respective emitting devices (2), are set side by side at a short distance from one another and have their other ends near to said panels (1); each of said channels (30) being formed in an external structure consisting of a set of partitions or layers (31) placed one on top of the other successively at pre-established distances.

9 Claims, 3 Drawing Sheets

APPARATUS FOR DETECTING INHOMOGENEITIES

FIELD OF THE INVENTION

The present invention relates to an apparatus for detecting inhomogeneities in panels or layers.

In particular, though not exclusively, it is of a type destined to be used for detecting inhomogeneities in panels realised by pressing of incoherent material of a woody type, which panels present the form of shavings or strands.

DESCRIPTION OF RELATED ART

This type of detection of inhomogeneity is already known, as in detecting delaminations of this type of panel while, after forming by pressing, the panels transit along a work line. The known apparatus comprise a plurality of ultrasound emitting devices, operating on a side of the transiting panel, and a corresponding plurality of ultrasound receiving devices, operating on the opposite side of the same panel at a predetermined distance from the emitting devices. The emitting devices are each connected and governed by a managing unit for activating the emitters. The receiving devices are each connected and governed by a unit for processing the signals detected by the receiving devices.

With the prior art it is possible to analyse the panel discretely, i.e. along longitudinal strips which correspond essentially to the position of the various "control channels", each of which is constituted by an emitting device and a corresponding receiving device that faces the emitting device and is located at the other side of the transiting panel.

With the prior art, in order to work in air without having direct contact between the transducers and the wood, the frequencies in use range from 20 kHz to 50 kHz. Higher frequencies would be attenuated far too rapidly by the air and internally of the wood material to be useful for detecting any defects in homogeneity, such as delamination.

At these frequencies the maximum dimension of inhomogeneity (delamination) that can be localised is about 25 mm. The minimum "visible" obstacle the sound waves can identify is about a quarter of the wave-length used, and, consequently, if we take a propagation velocity of the sound in the wood to be a maximum of 4000 m/s and a working frequency of 40 kHz, the dimension of the minimum detectable defect is 25 mm.

Since in the prior art each receiver is usually housed in a cylindrical container which occupies a certain volume of space, the density of the receivers is limited by the dimensions of the metal container. For structural and constructional reasons it is practically impossible, at a reasonable cost, to arrange a receiver every 25 mm (theoretical limit).

For containing a single receiver, the prior art uses a tube with walls clad with a sound-absorbent material. The material is however not free of cross-talk disturbance. This means that in the prior art it is not possible to near the receivers and transmitters too much as there would be interferences between contiguous control channels.

Further, these control devices leave "dark" areas, i.e. areas not controlled, which are in the zones between one "control channel" and another.

In particular, the size of these "dark zones" is inversely proportional to the distance between the single channels.

As sound pulses are used to examine the wood, and the analysis is done in the transiting direction of the wood generally about every 20 ms, in the prior art the cross-talk problem assumes such an importance with regard to the effectiveness of the control that in order to limit the risk of interference between adjacent pairs of sensors, a method often used is to activate the emitters and respective receivers alternately, thus accepting a considerable reduction (reaching 50%) of the extension of the zone truly analysed and controlled by the machine and therefore a consequent low overall reliability of the control.

SUMMARY OF THE INVENTION

The present invention aims to obviate the above-mentioned drawbacks according to what is set out in the claims.

BRIEF DESCRIPTION OF THE DRAWINGS

Further characteristics and advantages of the present invention will better emerge from the detailed description that follows, of some preferred but not exclusive embodiments of the invention, illustrated in the following by way of non-limiting example in the accompanying figures, in which.

DETAILED DESCRIPTION OF PREFERRED EMBODIMENTS OF THE INVENTION

Figure 1:
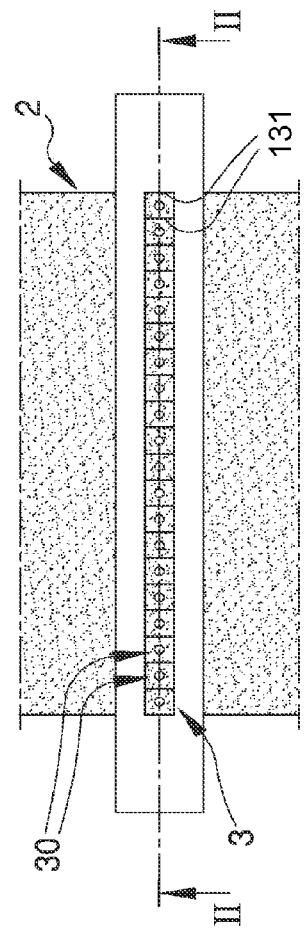
FIG. 1 illustrates a portion of a schematic plan view from above.
Figure 2:
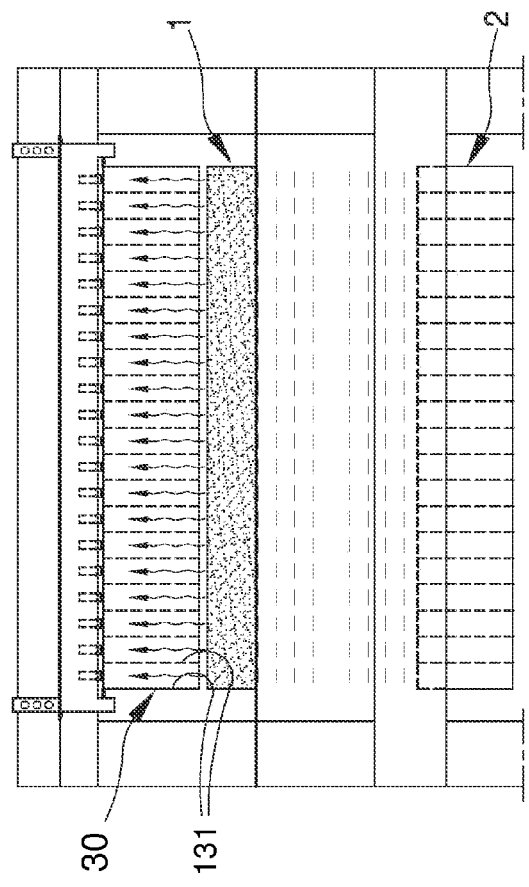
FIG. 2 is a schematic section performed along line II-II of FIG. 1.
Figure 3:
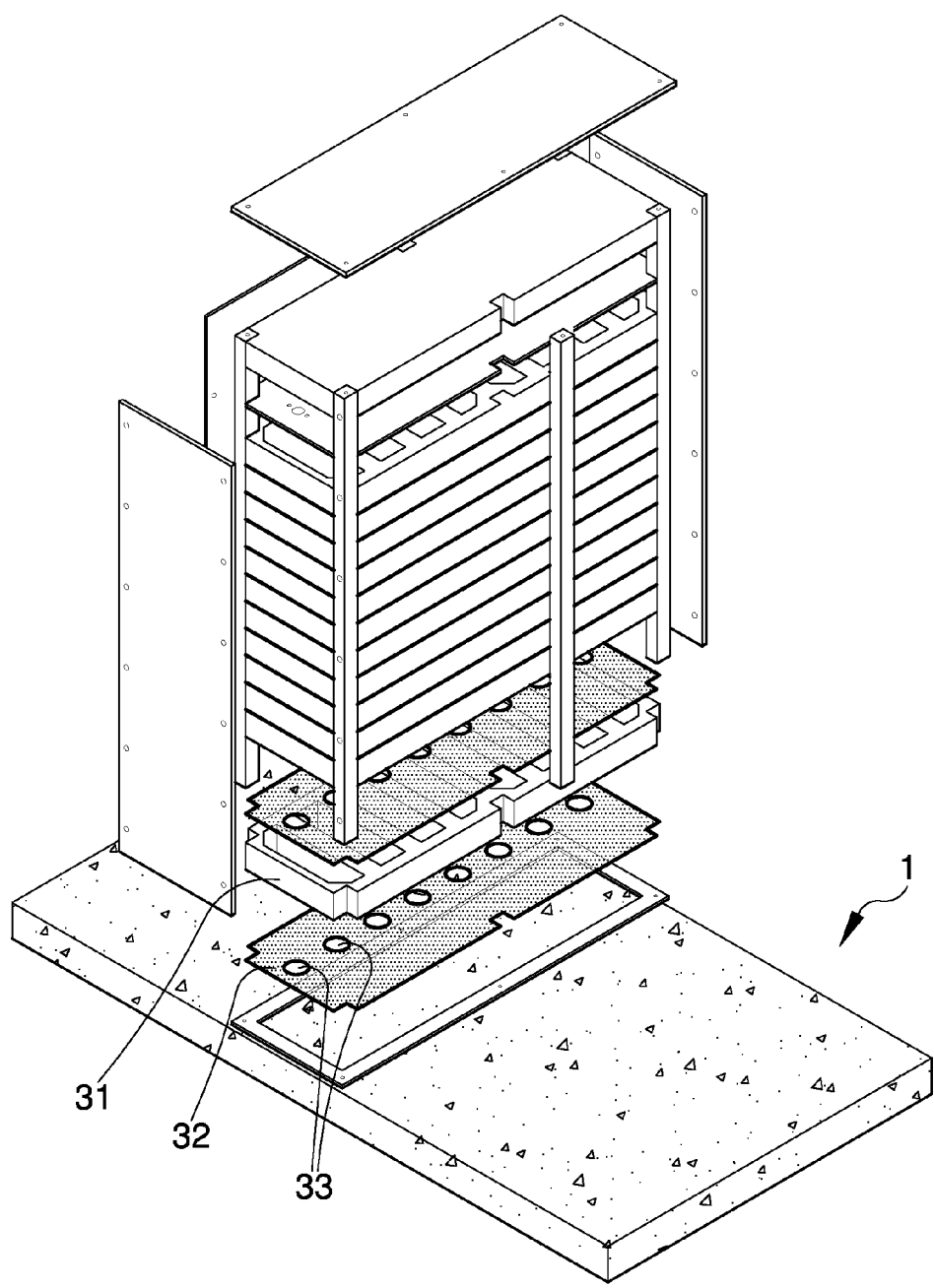
FIG. 3 is a schematic exploded view of the upper part.
Figure 4:
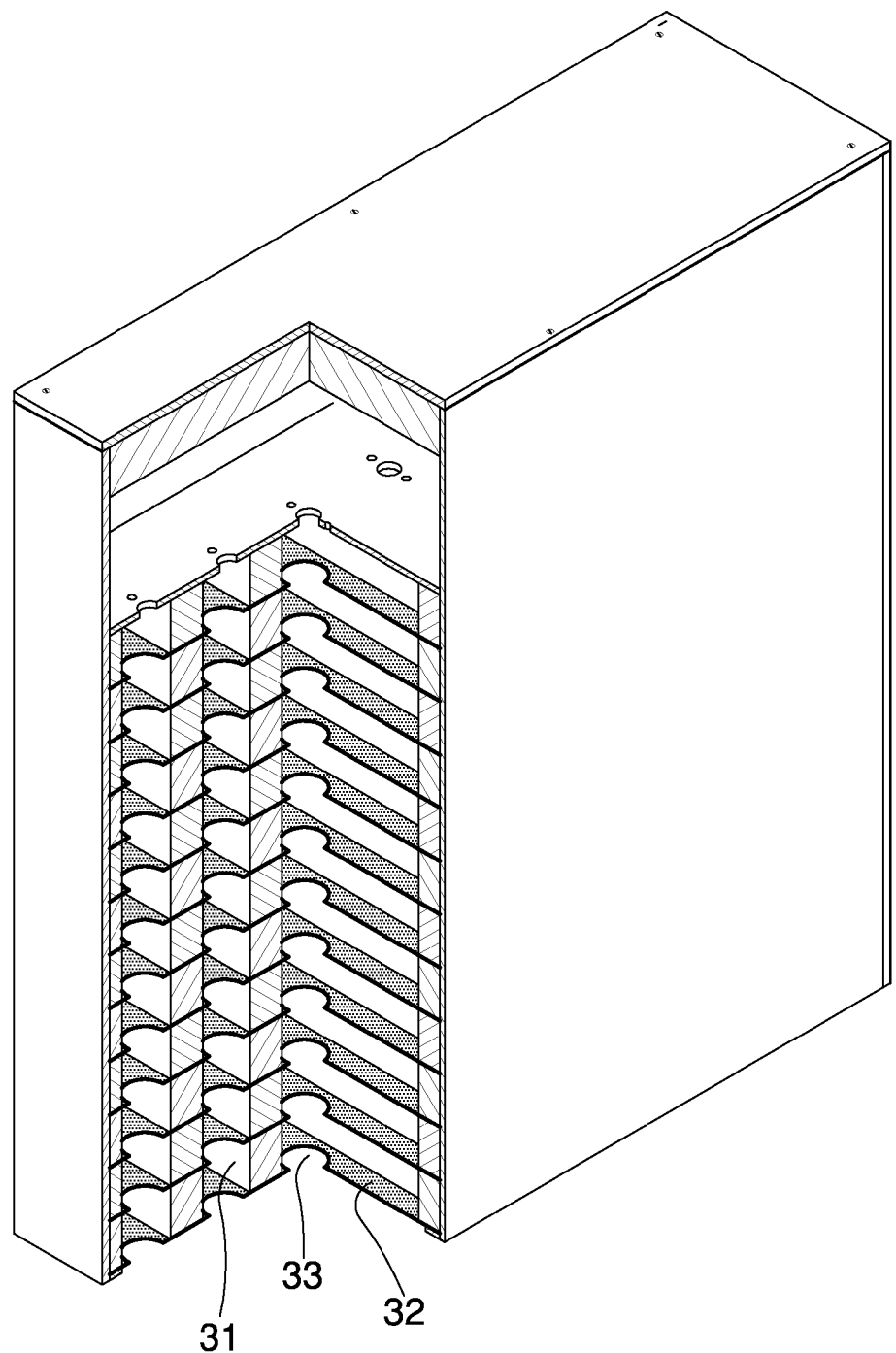
FIG. 4 is a schematic cutaway view.

With reference to the above-mentioned figures, 1 denotes a panel made by pressing of loose wood material such as wood shavings or strands or the like.

The panel 1 is in transit along a processing line, where it has recently been pressed. To detect inhomogeneities internally of the panel, which can be constituted by air bubbles, breaks or cracks (due to the presence of invisible defects such as air bubbles or internal cavities in the body, defective products are known as blisters in the sector), the apparatus of the invention is used. The apparatus essentially comprises a plurality of emitting devices 2 of sound waves, in particular ultrasonic sound waves, which operate from a side of the transiting panel 1, and a plurality of receiving devices 3 of sound waves, in particular of ultrasonic frequency, which operate on the opposite side of the same panel 1 at a predetermined distance from the emitting device 2.

The emitting and receiving devices, located at a predetermined distance from one another, are arranged aligned in a vertical direction, perpendicular to the panel 1 such that the propagating direction of the waves is practically perpendicular to the surface of the panel 1.

In particular, the receiving devices 3 are flanked consecutively at a short distance from one another along at least a strip or row that is transversal to the movement direction of the panel 1 and, obviously, parallel to the emitting devices 2.

The receiving devices 3 are situated at the ends of a plurality of channels 30 which are arranged aligned with the respective emitting devices 2 and are flanked at a short reciprocal distance, exhibiting the other ends thereof opposite to the ends housing the receiving devices 3, close to the single panels 1.

Each of the channels 30 is afforded in an assembly of partitions or layers 31 located superposed one successively to another at predetermined distances. In the illustrated embodiment of the figures, these layers are superposed in the shape of a pack.

The partitions or layers 31 are preferably made of a sound-absorbent material.

At least a sheet, preferably made of polycarbonate 32, is interposed between at least two contiguous partitions or layers 31, in which holes 33 are afforded for identifying an area of free passage of the waves emitted by the emitting devices 2. The interposing of the polycarbonate sheets 32 is preferably actuated between a partition or layer 31 and an adjacent partition or layer 31.

In particular, the holes 33 are calibrated and normally aligned with each emitting device 2 such as to identify a sort of guide conduit which directly leads to the relative receiving device 3.

The receiving devices 3 are furthermore acoustically insulated from one another by means of foils having separator 131 functions, which foils extend such as to create chambers that are open at ends thereof up to a predetermined distance from the panel 1.

The ability of the apparatus to adequately cover the surface to be controlled can be increased by reducing the distance between two receivers 3 or consecutively contiguous sensors, calculated in a transversal direction to the transit direction of the panels 1 to be controlled, and brought easily to the desired resolution level of 25 mm, using, for example, three parallel rows of receivers 3 or sensors arranged such that the receivers 3 or sensors of the rows are suitably "staggered" in such a way as to realise ideal corridors of a width which exactly corresponds to the distance of 25 mm corresponding to the dimension of the minimum defect detectable with a sound propagation velocity maximum of 4000 m/s and a working frequency of 40 kHz.

With the arrangement on three parallel rows, the distance between two consecutive receivers 3 or sensors is 75 mm in each row or strip.

The receivers 3 or sensors (and the corresponding emitters 2) are distributed on the three rows such that the ones in each row are staggered, i.e. distanced in a transversal direction, by 25 mm with respect to those of the contiguous row. As already mentioned, with a frequency of 40 KHz, the transversal distance of 25 mm provides optimal cover while at the same time maintaining a distance between the contiguous sensors which facilitates reduction of the cross-talk phenomenon.

The emitting devices are connected to and governed by one only managing unit for activating the emitters. The receiving devices are connected to and governed by one only unit for processing the signals detected by the receiving devices themselves.

The described apparatus enables actuating a method for detecting inhomogeneity in panels or layers, realised by pressing of wood materials. In particular the method is suitable for being used for panels 1 transiting along a work line by use of an apparatus comprising emitting devices 2 of ultrasound waves, operating on a side of the panel 1 in transit, and corresponding receiving devices 3 of ultrasound waves, operating on the opposite side of the panel 1 at a predetermined distance from the relative emitting devices 2.

The minimising of the interference phenomenon ("cross-talk") between adjacent pairs of sensors is actuated by means of the partitions which trap the sound coming from emitters which are not directly facing the sensor and transform it into heat (receivers and emitters) in respect to which the receiving devices 3 are situated at the ends of a plurality of channels 30, which are arranged aligned with the respective emitting devices 2, flanked at a short reciprocal distance, and exhibit other ends thereof close to the panels 1.

The channels 30 are fashioned internally of a single external structure, arranged flanked to one another at a short reciprocal distance, the distance corresponding to the distance between the emitting devices 2 aligned with the respective receiving devices 3.

The external structure, and therefore also each of the channels 30, is constituted by an assembly of sound-absorbent partitions or layers 31 located superposed one successively on another at predetermined distances, usually in the shape of a pack. Sheets, preferably polycarbonate sheets 32, are further interposed between at least two adjacent layers 31, or more frequently between a layer 31 and another; holes 33 are afforded in the sheets 32, which holes are calibrated and aligned with each emitting device 2, for identifying an area of free passage of the waves emitted by the emitting devices 2.

In the present invention the sensors can be positioned at a short distance from one another and placed directly on a printed circuit, which consequently mechanically enables densities to be reached which previously were unimaginable. The problem of cross-talk has been eliminated by use of partitions easily fashioned using layers of sound-absorbent material alternated with sheets of plexiglass. This structure exhibits very much reduced production costs with respect to the use of a plurality of mechanically distinct tubes, which each require a metal casing coated with sound-absorbent material, a supply cable and a dedicated printed circuit.

Differently from the prior art illustrated herein above, the described device enables considerably nearing the detecting channels (and integrating them in a single structure), possibly grouping them in sub-groups such as to use a single casing provided with partitions realised in sound-absorbent material that is easy to shape, and inexpensive.

The further implies the possibility of using a single supply cable in a single printed circuit for each group of emitters/receivers.

The partitions further transform the sound emitted into air by the transmitters into heat, and reduce the duration of the pulse itself; this enables a reduction in time between one pulse and another from 20 ms to 3 ms.

The use of partitions and this mechanical structure enables a high density of discrimination by the receiving device 3 coaligned with the corresponding emitting device 2, such that the signaling of any defect or delamination is easily identifiable by the position of the emitter-receiver pair involved.

Precisely because of the way it is constructed, the structure further enables reducing the relative distances to a minimum (obviously, as well as the distances of the corresponding emitting devices) and also realises an excellent resolution capacity in terms of distance between possible defects.

Further, the invention provides the advantage of maximising the probability of detecting defects.

Further advantages are of an economic type and include reduction of the times of installation and maintenance of the reduction of the plant construction costs.

The invention claimed is:

1. An apparatus for detecting inhomogeneities in panels, of the type suitable to be used for panels (1) in transit along a processing line and comprising a plurality of sound wave emitting devices (2), operating from one side of the panel (1) in transit, and a plurality of sound wave receiving devices (3), operating from the opposite side of the same panel (1) at a pre-established distance from the emitting devices (2), characterised in that said receiving devices (3) are situated at the ends of a plurality of channels (30), which are disposed in alignment with the respective emitting devices (2), are set side by side at a short distance from one another and have their other ends near to said panels (1); each of said channels (30) extending between its respective receiving device (3) and the panel (1) in transit and being formed in an external structure comprising a set of partitions or layers (31) spaced apart from each other and placed one on top of the other successively at pre-established distances, further characterized in that between at least two of said partitions or layers (31) there is interposed a sheet of solid material (32) in which there are formed holes (33) for defining the area of free passage of the waves of said emitting devices.

2. The apparatus according to claim 1, characterised in that said partitions or layers (31) are made of sound-absorbing material.

3. The apparatus according to claim 2, characterised in that said sheet of solid material comprises polycarbonate.

4. The apparatus according to claim 1, characterised in that said sheet of solid material comprises polycarbonate.

5. The apparatus according to claim 4, characterised in that said holes (33) are calibrated and aligned with each emitting device (2).

6. The apparatus according to claim 5, characterised in that said receivers or sensors (3) are acoustically insulated from one another by means of foils having the function of a separator and which extend so as to create chambers open at the ends up to a pre-established distance from the panel (1).

7. The apparatus according to claim 6, characterised in that the distance between two consecutive adjacent receivers or sensors is approximately 25 mm and that the frequency of the emitted wave is 40 kHz.

8. The apparatus according to claim 1, wherein the external structure comprises at least three partitions or layers (31).

9. A method for detecting inhomogeneities in panels (1) in transit along a processing line comprising a step of using ultrasound wave emitting devices (2), operating on one side of the panel (1) in transit, and corresponding ultrasound wave receiving devices (3), operating on the opposite side of the same panel (1) at a pre-established distance from the respective emitting devices (2), wherein said receiving devices (3) are situated at the ends of a plurality of channels (30), which are disposed in alignment with the respective emitting devices (2), set side by side at a short distance from one another and have their other ends near to said panels (1); each of said channels (30) being formed in an external structure consisting of a set of sound-absorbing partitions or layers (31) placed one on top of the other successively at pre-established distances; there being interposed between said partitions or layers (31) polycarbonate sheets (32) in which there are formed holes (33), calibrated and aligned with each emitting device (2), for defining an area of free passage of the waves emitted by said emitting devices (2).

\* \* \* \* \*